US012667384B2

(12) United States Patent
Howell

(10) Patent No.: US 12,667,384 B2
(45) Date of Patent: Jun. 30, 2026

(54) SPLITABLE TISSUE-CUTTING DEVICES, ASSEMBLIES, AND METHODS

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 407 days.

(21) Appl. No.: 18/116,748

(22) Filed: Mar. 2, 2023

(65) Prior Publication Data

US 2023/0277212 A1 Sep. 7, 2023

Related U.S. Application Data

(60) Provisional application No. 63/316,279, filed on Mar. 3, 2022.

(51) Int. Cl.
*A61B 17/3209* (2006.01)
*A61B 17/00* (2006.01)

(52) U.S. Cl.
CPC .................. *A61B 17/32093* (2013.01); *A61B 2017/00526* (2013.01); *A61B 2017/00836* (2013.01)

(58) Field of Classification Search
CPC ........... A61B 2017/32113; A61B 2017/00469; A61B 17/32093; A61B 17/3415; A61M 25/06; A61M 25/09041; A61M 25/01; A61M 25/0612; A61M 25/0637; A61M 25/065; A61M 2025/0681
See application file for complete search history.

(56) References Cited

U.S. PATENT DOCUMENTS 2,566,499 A 9/1951 Richter
2,842,133 A 7/1958 Antoni
(Continued)

FOREIGN PATENT DOCUMENTS

CN 2456639 Y 10/2001
CN 210844555 U 6/2020
(Continued)

OTHER PUBLICATIONS

PCT/US2021/059256 filed Nov. 12, 2021 International Search Report and Written Opinion dated Mar. 23, 2022.
(Continued)

*Primary Examiner* — Katherine H Schwiker
(74) *Attorney, Agent, or Firm* — Rutan & Tucker LLP

(57) ABSTRACT

Tissue-cutting devices and methods thereof, where a tissue-cutting device is coupleable with a catheter. The tissue-cutting device includes a blade that cuts the skin during insertion of the device in a needle track to enlarge to needle tract. The tissue-cutting device is configured for lateral separation from the catheter and/or a guidewire. The tissue-cutting device includes a channel for receiving the catheter and/or a guidewire. The channel can be configured to (i) retain the catheter/guidewire within the channel in the absence of a deliberate action by the clinician and (ii) facilitate lateral removal of the catheter/guidewire from the channel in response to the deliberate action. A catheter assembly includes a catheter coupled with the tissue-cutting device. The tissue-cutting device may include a sheath extending along a distal portion of the tissue-cutting device.

23 Claims, 6 Drawing Sheets

(56) References Cited

U.S. PATENT DOCUMENTS

| | | | |
|---|---|---|---|
| 3,921,631 A | | 11/1975 | Thompson |
| 4,324,044 A | * | 4/1982 | Shahinian, Jr. ....... A61F 9/0133 |
| | | | 30/294 |
| 4,392,856 A | * | 7/1983 | Lichtenstein ..... A61M 25/0637 |
| | | | 604/177 |
| 4,601,710 A | | 7/1986 | Moll |
| 4,693,250 A | | 9/1987 | Coons |
| 4,889,112 A | | 12/1989 | Schachner et al. |
| 4,955,890 A | | 9/1990 | Yamamoto et al. |
| 5,098,393 A | * | 3/1992 | Amplatz .......... A61M 39/0606 |
| | | | 604/167.03 |
| 5,279,285 A | | 1/1994 | Griggs |
| 5,334,157 A | * | 8/1994 | Klein ............... A61M 25/0637 |
| | | | 604/165.03 |
| 5,509,900 A | | 4/1996 | Kirkman |
| 5,578,009 A | | 11/1996 | Kraus et al. |
| 5,728,073 A | | 3/1998 | Whisson |
| 5,755,697 A | | 5/1998 | Jones et al. |
| 5,800,450 A | | 9/1998 | Lary et al. |
| 5,843,115 A | | 12/1998 | Morejon |
| 6,033,388 A | | 3/2000 | Nordstrom et al. |
| 6,517,519 B1 | | 2/2003 | Rosen et al. |
| 6,544,277 B1 | | 4/2003 | O'Heeron et al. |
| 6,761,725 B1 | | 7/2004 | Grayzel et al. |
| 9,114,227 B2 | | 8/2015 | Blanchard |
| 9,480,498 B1 | | 11/2016 | Kessler |
| 10,028,762 B1 | | 7/2018 | Slupchynskyj |
| 10,188,403 B2 | | 1/2019 | Mirochinik et al. |
| 10,376,675 B2 | | 8/2019 | Mitchell et al. |
| 10,603,071 B1 | | 3/2020 | Whitman et al. |
| 2002/0040231 A1 | * | 4/2002 | Wysoki ............... A61M 25/065 |
| | | | 606/185 |
| 2002/0161387 A1 | | 10/2002 | Blanco |
| 2002/0165600 A1 | * | 11/2002 | Banas ................... A61M 25/09 |
| | | | 600/585 |
| 2002/0177864 A1 | | 11/2002 | Camrud |
| 2003/0074013 A1 | * | 4/2003 | Schooler ............ A61B 17/3213 |
| | | | 606/167 |
| 2004/0133227 A1 | | 7/2004 | Shang et al. |
| 2004/0181246 A1 | | 9/2004 | Heppler |
| 2004/0181273 A1 | | 9/2004 | Brasington et al. |
| 2005/0177183 A1 | | 8/2005 | Thorne et al. |
| 2009/0024089 A1 | | 1/2009 | Levine et al. |
| 2009/0076435 A1 | | 3/2009 | Melsheimer et al. |
| 2009/0125030 A1 | | 5/2009 | Tebbe et al. |
| 2010/0057056 A1 | | 3/2010 | Gurtner et al. |
| 2012/0130417 A1 | | 5/2012 | Lepulu et al. |
| 2012/0226299 A1 | | 9/2012 | Heppler |
| 2013/0197558 A1 | * | 8/2013 | Ingold, Jr. ........ A61B 17/32093 |
| | | | 606/185 |
| 2016/0128713 A1 | | 5/2016 | Rauchwerger et al. |
| 2016/0220786 A1 | | 8/2016 | Mitchell et al. |
| 2016/0346503 A1 | | 12/2016 | Jackson et al. |
| 2017/0128700 A1 | | 5/2017 | Roche Rebollo |
| 2017/0296792 A1 | | 10/2017 | Ornelas Vargas et al. |
| 2019/0307485 A1 | | 10/2019 | Kiev |
| 2019/0351183 A1 | | 11/2019 | Ishida |
| 2020/0061322 A1 | | 2/2020 | De Rezende Neto |
| 2020/0086095 A1 | | 3/2020 | Kleinhaus |
| 2020/0155190 A1 | | 5/2020 | Basadonna et al. |
| 2020/0222077 A1 | | 7/2020 | Takahashi |
| 2020/0246597 A1 | | 8/2020 | Broniec et al. |
| 2021/0069471 A1 | | 3/2021 | Howell |
| 2021/0085927 A1 | | 3/2021 | Howell |
| 2021/0106351 A1 | | 4/2021 | Hossack et al. |
| 2021/0113809 A1 | | 4/2021 | Howell |
| 2021/0113810 A1 | | 4/2021 | Howell |
| 2021/0121661 A1 | | 4/2021 | Howell |
| 2021/0212722 A1 | | 7/2021 | Kiev et al. |
| 2022/0087708 A1 | | 3/2022 | Chen et al. |
| 2022/0152368 A1 | | 5/2022 | Thornley et al. |
| 2022/0176081 A1 | | 6/2022 | Spataro et al. |
| 2023/0141739 A1 | | 5/2023 | Doctor et al. |
| 2023/0233227 A1 | | 7/2023 | Lindekugel et al. |
| 2023/0241353 A1 | | 8/2023 | Howell et al. |
| 2023/0241354 A1 | | 8/2023 | Howell |
| 2023/0255660 A1 | | 8/2023 | Howell |
| 2023/0255661 A1 | | 8/2023 | Howell |
| 2023/0277813 A1 | | 9/2023 | Howell |
| 2023/0277814 A1 | | 9/2023 | Howell |
| 2025/0381370 A1 | | 12/2025 | Spataro et al. |

FOREIGN PATENT DOCUMENTS

| | | |
|---|---|---|
| CN | 111481303 A | 8/2020 |
| CN | 112155683 A | 1/2021 |
| DE | 10100332 A1 | 7/2002 |
| DE | 202004012605 U1 | 10/2004 |
| WO | 9108709 A1 | 6/1991 |
| WO | 9412091 A1 | 6/1994 |
| WO | 02087666 A2 | 11/2002 |
| WO | 03022129 A2 | 3/2003 |
| WO | 2011024013 A1 | 3/2011 |
| WO | 2011057282 A2 | 5/2011 |
| WO | 2012087506 A2 | 6/2012 |
| WO | 2016176065 A1 | 11/2016 |
| WO | 2017006323 A1 | 1/2017 |
| WO | 2020076691 A1 | 4/2020 |
| WO | 2022104149 A1 | 5/2022 |
| WO | 2022120201 A1 | 6/2022 |
| WO | 2023081465 A1 | 5/2023 |
| WO | 2023122313 A1 | 6/2023 |
| WO | 2023141170 A1 | 7/2023 |
| WO | 2023150263 A1 | 8/2023 |
| WO | 2023150314 A1 | 8/2023 |
| WO | 2023158643 A1 | 8/2023 |
| WO | 2023158645 A1 | 8/2023 |
| WO | 2023167943 A1 | 9/2023 |
| WO | 2023168005 A1 | 9/2023 |
| WO | 2023168097 A1 | 9/2023 |

OTHER PUBLICATIONS

PCT/US2021/061857 filed Dec. 3, 2021 International Search Report and Written Opinion dated Apr. 11, 2022.

Rauchwerger, Jacob Jeffrey, Michael Serle, and Jeffrey C. Astbury. "Novel Wire-Guided Scalpel to Facilitate Central Venous Catheter Insertion without a Skin Bridge." Vascular Specialist International 37 (2021).

U.S. Appl. No. 17/542,096, filed Dec. 3, 2021 Restriction Requirement dated Mar. 1, 2023.

PCT/US2023/012270 filed Feb. 3, 2023 International Search Report and Written Opinion dated Jun. 21, 2023.

PCT/US2023/012345 filed Feb. 3, 2023 International Search Report and Written Opinion dated Jun. 27, 2023.

PCT/US2023/013056 filed Feb. 14, 2023 International Search Report and Written Opinion dated Jun. 12, 2023.

PCT/US2023/013058 filed Jun. 7, 2023 International Search Report and Written Opinion dated Jun. 7, 2023.

PCT/US2023/014384 filed Mar. 2, 2023 International Search Report and Written Opinion dated Jun. 16, 2023.

PCT/US2023/014532 filed Mar. 3, 2023 International Search Report and Written Opinion dated Jul. 10, 2023.

PCT/US2022/049134 filed Nov. 7, 2022 International Search Report and Written Opinion dated Mar. 30, 2023.

PCT/US2022/053889 filed Dec. 22, 2022 International Search Report and Written Opinion dated Apr. 20, 2023.

PCT/US2023/011067 filed Jan. 18, 2023 International Search Report and Written Opinion dated May 11, 2023.

PCT/US2023/014298 filed Mar. 1, 2023 International Search Report and Written Opinion dated Jun. 1, 2023.

U.S. Appl. No. 17/542,096, filed Dec. 3, 2021 Non Final Office Action dated Jun. 1, 2023.

U.S. Appl. No. 17/525,774, filed Nov. 12, 2021 Non-Final Office Action dated Jan. 24, 2024.

U.S. Appl. No. 17/542,096, filed Dec. 3, 2021 Advisory Action dated Nov. 29, 2023.

U.S. Appl. No. 17/542,096, filed Dec. 3, 2021 Final Office Action dated Sep. 20, 2023.

(56)        References Cited

OTHER PUBLICATIONS

U.S. Appl. No. 17/542,096, filed Dec. 3, 2021 Non-Final Office Action dated Jan. 18, 2024.

U.S. Appl. No. 17/525,774, filed Nov. 12, 2021 Advisory Action dated Aug. 26, 2024.

U.S. Appl. No. 17/525,774, filed Nov. 12, 2021 Final Office Action dated Jun. 18, 2024.

U.S. Appl. No. 17/542,096, filed Dec. 3, 2021 Final Office Action dated Aug. 1, 2024.

U.S. Appl. No. 17/525,774, filed Nov. 12, 2021 Non-Final Office Action dated Jan. 28, 2025.

U.S. Appl. No. 17/525,774, filed Nov. 12, 2021 Notice of Allowance dated Jul. 18, 2025.

U.S. Appl. No. 17/542,096, filed Dec. 3, 2021 Non-Final Office Action dated Dec. 27, 2024.

U.S. Appl. No. 17/542,096, filed Dec. 3, 2021 Notice of Allowance dated May 9, 2025.

U.S. Appl. No. 17/982,119 filed Nov. 7, 2022 Non-Final Office Action dated Aug. 13, 2025.

U.S. Appl. No. 17/982,119 filed Nov. 7, 2022 Restriction Requirement dated May 5, 2025.

U.S. Appl. No. 18/098,607, filed Jan. 18, 2023 Final Office Action dated Aug. 11, 2025.

U.S. Appl. No. 18/098,607, filed Jan. 18, 2023 Non-Final Office Action dated Feb. 6, 2025.

U.S. Appl. No. 18/109,793, filed Feb. 14, 2023 Restriction Requirement dated Jul. 17, 2025.

U.S. Appl. No. 18/105,357, filed Feb. 3, 2023 Non-Final Office Action dated Oct. 2, 2025.

U.S. Appl. No. 18/105,743, filed Feb. 3, 2023 Non-Final Office Action dated Oct. 2, 2025.

U.S. Appl. No. 18/109,793, filed Feb. 14, 2023 Non-Final Office Action dated Oct. 1, 2025.

U.S. Appl. No. 18/117,334, filed Mar. 3, 2023 Restriction Requirement dated Oct. 30, 2025.

U.S. Appl. No. 17/982,119, filed Nov. 7, 2022 Notice of Allowance dated Feb. 27, 2026.

U.S. Appl. No. 18/087,699, filed Dec. 22, 2022 Final Office Action dated Feb. 13, 2026.

U.S. Appl. No. 18/105,357, filed Feb. 3, 2023 Final Office Action dated Feb. 13, 2026.

U.S. Appl. No. 18/109,793, filed Feb. 14, 2023 Notice of Allowance dated Mar. 5, 2026.

U.S. Appl. No. 18/116,249, filed Mar. 1, 2023 Restriction Requirement dated Feb. 5, 2026.

U.S. Appl. No. 18/117,334, filed Mar. 3, 2023 Non-Final Office Action dated Mar. 26, 2026.

* cited by examiner

PROXIMAL

DISTAL

FIG. 2A
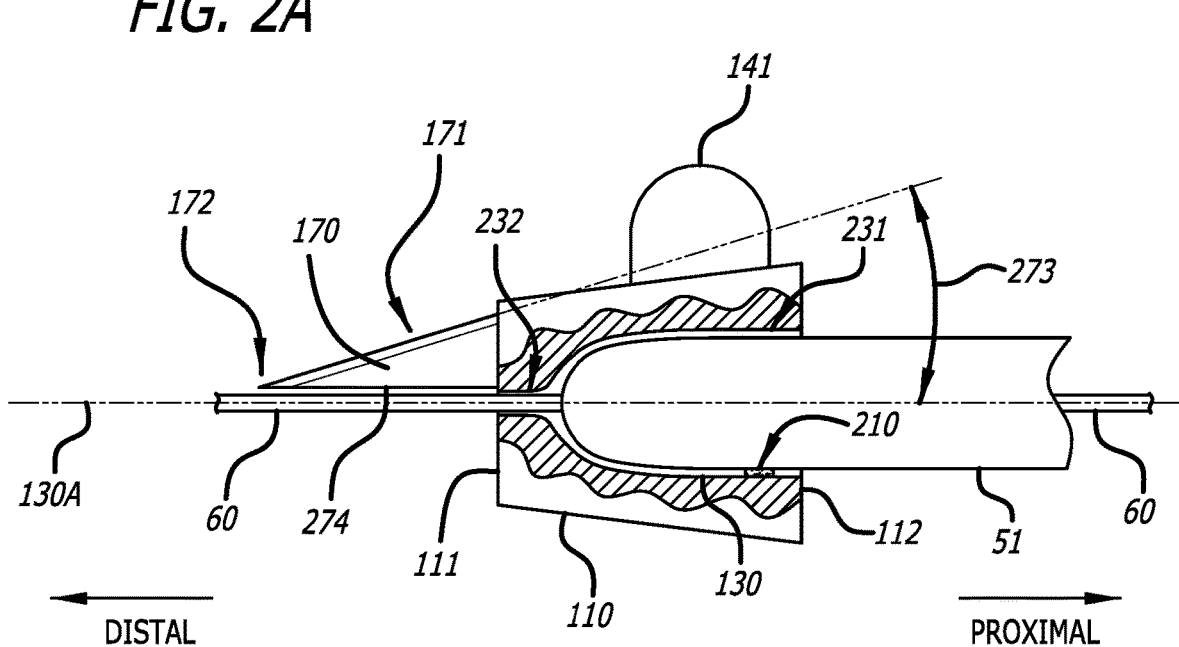
DISTAL ←
PROXIMAL →
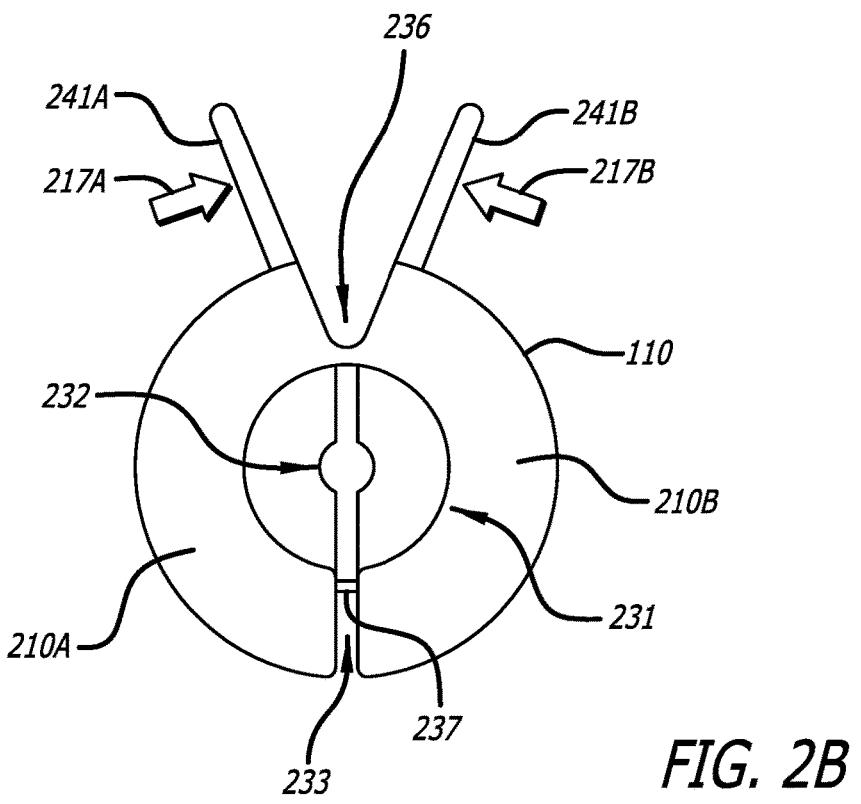
FIG. 2B

SPLITABLE TISSUE-CUTTING DEVICES, ASSEMBLIES, AND METHODS

PRIORITY

This application claims the benefit of priority to U.S. Provisional Application No. 63/316,279, filed Mar. 3, 2022, which is incorporated by reference in its entirety into this application.

BACKGROUND

Before placing a catheter in a blood vessel of a patient, it is common to nick the patient's skin about a needle tract at an insertion site for dilation of tissue therearound with a dilator. Typically, nicking the patient's skin and dilating the tissue around the needle tract is performed separately. Indeed, the nicking is usually performed with a dedicated skin nicker or a scalpel having a #11 blade; the dilating is usually performed with a dilator two French sizes larger than the catheter being placed. Attempts to integrate the nicking of the patient's skin and the dilating of the tissue around the needle tract have resulted in a spring-loaded blade generally regarded as unsafe due to clinicians not being able to control the blade. What is needed is a tissue-cutting device that safely integrates the nicking of a patient's skin at an insertion site with the dilating of tissue around a needle tract at the insertion site. Such a device would reduce procedural time and errors when, for example, placing a catheter at the insertion site.

Disclosed herein are tissue-cutting devises, assemblies, and methods that address the foregoing.

SUMMARY

Disclosed herein a tissue-cutting device that, according to some embodiments, includes a body defining a distal end and a proximal end, where the body includes a channel extending longitudinally along the body between the distal end and the proximal end, and the channel is configured to receive a vascular catheter therein. A tissue-cutting blade is attached to the body, where the blade extends distally away from the distal end, and extends laterally away from a longitudinal axis of the channel such that a cutting edge of the blade is disposed opposite the longitudinal axis.

In some embodiments, the device is configured for insertion along a needle tract extending between a skin surface and a blood vessel wall of a patient, and the blade is configured to cut a skin of a patient during insertion of the device to enlarge the needle tract.

In some embodiments, the distal end of the body provides an insertion stop for the device during insertion of the device. A cutting edge of the blade may be disposed at an angle with respect to the longitudinal axis of the channel so that a distal portion of the cutting edge is closer to the longitudinal axis than a proximal portion of the cutting edge. In some embodiments, the insertion stop defines a depth of cut for the blade in accordance with the angle of the cutting edge.

The body may include one or more protrusions extending laterally away from the body and in some embodiments, the protrusions define a handle for the device.

The blade may be formed of a stainless steel, and the body may be formed of a thermo-plastic material via an injection molding process. In some embodiments, the blade is insert-molded into the body.

In some embodiments, the body includes a sheath extending distally away from the distal end and the body, where (i) the sheath extends along the blade, (ii) the channel extends along the sheath, and (iii) a sharp distal tip of the blade is insert-molded into a wall of the sheath. In some embodiments, the sheath includes a taper such that insertion of the sheath within the needle track dilates the needle track.

The device may be configured to (i) allow lateral decoupling of the device from a catheter in response to a deliberate action by a clinician, and (ii) inhibit lateral decoupling the device from the catheter in the absence of the deliberate action by the clinician.

In some embodiments, the body includes a first body side coupled to a second body side via a longitudinally oriented hinge, where the channel is disposed between the first body side and the second body side. In some embodiments, rotation of the second body side with respect to the first body side transitions the channel between a closed state and an open state, where the catheter is laterally constrained within the channel in the closed state, and the catheter is laterally removable from the channel in the open state. In some embodiments, the hinge is a living hinge is formed via the injection molding process.

In some embodiments, a first protrusion of the one or more protrusions extends away from the first body side, a second protrusion of the one or more protrusions extends away from the second body side, and applying a squeezing force to the first and second protrusions transitions the channel from the closed state to the open state.

In some embodiments, the body includes one or more frangible connecting members extending between the first body side and the second body side at a location opposite the hinge, such that the one or more frangible connecting members constrain the channel in the closed state, and applying the squeezing force breaks the one or more frangible connecting members.

In some embodiments, the device further includes a blade cover selectively transitionable between a safety state and a use state, wherein the blade cover (i) extends over the cutting edge in the safety state, and (ii) is disposed away from the cutting edge in the use state. In some embodiments, the blade cover is rotatably coupled with the body, and transitioning the blade cover away from the safety state toward the use state includes rotating the blade cover away from the cutting edge. In some embodiments, rotation of the blade cover away from the safety state is inhibited by a detent.

Also disclosed herein is a catheter assembly, that includes a catheter configured for advancement along a vasculature of a patient, and a tissue-cutting device, according to any of the embodiments summarized above, coupled with the catheter.

In some embodiments, the tissue-cutting device is attached to the catheter adjacent a diameter transition portion of the catheter. In some embodiments, the tissue-cutting device is attached to the catheter adjacent a distal end of the catheter. In some embodiments, the tissue-cutting device is attached to the catheter via an adhesive.

In some embodiments, during use, manipulation of the catheter is facilitated by grasping the tissue-cutting device.

Also disclosed herein is a method for placing a catheter into a vasculature of a patient, that includes (i) inserting a needle into the patient from a skin surface to a blood vessel lumen to define a needle tract; (ii) inserting a guidewire into the vasculature of the patient via the needle tract; (iii) advancing the catheter along the guidewire, where the catheter includes a catheter tube having a tissue-cutting device attached thereto; (iv) inserting the tissue-cutting device into the needle tract such that a blade of the tissue-cutting device cuts the skin adjacent the needle tract to enlarge the needle tract; (v) laterally decoupling the tissue-cutting device from the catheter; and (vi) advancing the catheter along the vasculature.

In some embodiments of the method, the tissue-cutting device includes a body defining a distal end and a proximal end, where the body includes a channel extending between the distal end and the proximal end, and where the catheter tube is disposed within the channel.

In some embodiments of the method, the blade extends distally away from the distal end of the body of the tissue-cutting device, such that the blade extends distally along a longitudinal axis of the channel so that the blade extends along the guidewire during use, and a cutting edge of the blade is disposed opposite the longitudinal axis.

In some embodiments of the method, the cutting edge is disposed at an angle with respect to the guidewire so that a depth of cut is defined by an insertion depth of the device within the needle tract. In some embodiments, the distal end of the body defines an insertion stop for the tissue-cutting device, and inserting the tissue-cutting device into the needle tract includes abutting the insertion stop against a skin surface of the patient.

In some embodiments of the method, the device includes a sheath coupled with the body, where the sheath extends distally away from the distal end of the body, and where the channel extends along the sheath. In some embodiments of the method, a sharp distal tip of the blade is disposed within a wall of the sheath.

In some embodiments of the method, the sheath includes a taper configured to dilate the needle tract during insertion of the sheath within the needle tract.

In some embodiments of the method, the device includes a blade cover selectively transitionable between a safety state and a use state, where the blade cover extends over the cutting edge in the safety state and the blade cover is disposed away from the cutting edge in the use state, and the method further includes transitioning the blade cover away from the safety state toward the use state. In some embodiments of the method, the blade cover is rotatably coupled with the body, and transitioning the blade cover from the safety state to the use state includes rotating the blade cover away from the cutting edge.

In some embodiments of the method, the body includes a first body side coupled with a second body side via a longitudinally oriented hinge, and the channel is disposed between the first body side and the second body side. According to such embodiments, rotation of the second body side with respect to the first body side transitions the channel between a closed state and an open state, where the catheter is laterally constrained within the channel in the closed state and the catheter is laterally removable from the channel in the open state.

In some embodiments of the method, the first body side includes a first lateral protrusion and the second body side includes a second lateral protrusion, and the method further includes applying a squeezing force to the first and second protrusions to transition the channel from the closed state to the open state.

In some embodiments, the method may further include laterally removing the guidewire from the channel in the open state.

These and other features of the concepts provided herein will become more apparent to those of skill in the art in view of the accompanying drawings and following description, which describe particular embodiments of such concepts in greater detail.

DRAWINGS

FIG. 2A is a side view of the tissue-cutting device of FIG. 1A, in accordance with some embodiments.

FIG. 2B is a back view of the tissue-cutting device of FIG. 1A disposed in a closed state, in accordance with some embodiments.

DESCRIPTION

Figure 1A:
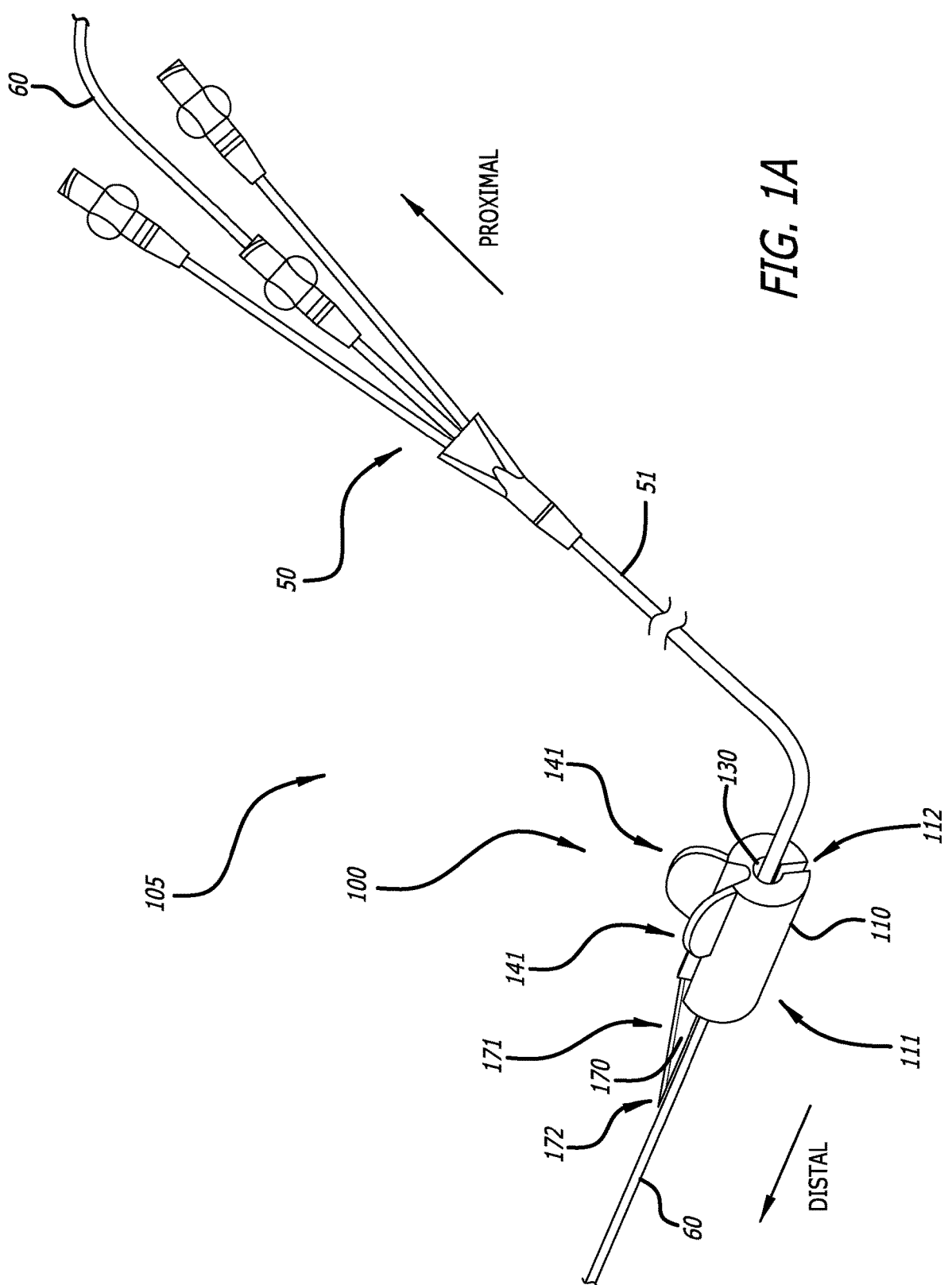
FIG. 1A illustrates a tissue-cutting device coupled with a catheter, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a tissue-cutting device includes a portion or section of the tissue-cutting device intended to be near a clinician when the tissue-cutting device is used on a patient. Likewise, a "proximal length" of, for example, the tissue-cutting device includes a length of the tissue-cutting device intended to be near the clinician when the tissue-cutting device is used on the patient. A "proximal end" of, for example, the tissue-cutting device includes an end of the tissue-cutting device intended to be near the clinician when the tissue-cutting device is used on the patient. The proximal portion, the proximal section, or the proximal length of the tissue-cutting device can include the proximal end of the tissue-cutting device; however, the proximal portion, the proximal section, or the proximal length of the tissue-cutting device need not include the proximal end of the tissue-cutting device. That is, unless context suggests otherwise, the proximal portion, the proximal section, or the proximal length of the tissue-cutting device is not a terminal portion or terminal length of the tissue-cutting device.

With respect to "distal," a "distal portion" or a "distal section" of, for example, a tissue-cutting device includes a portion or section of the tissue-cutting device intended to be near or in a patient when the tissue-cutting device is used on the patient. Likewise, a "distal length" of, for example, the tissue-cutting device includes a length of the tissue-cutting device intended to be near or in the patient when the tissue-cutting device is used on the patient. A "distal end" of, for example, the tissue-cutting device includes an end of the tissue-cutting device intended to be near or in the patient when the tissue-cutting device is used on the patient. The distal portion, the distal section, or the distal length of the tissue-cutting device can include the distal end of the tissue-cutting device; however, the distal portion, the distal section, or the distal length of the tissue-cutting device need not include the distal end of the tissue-cutting device. That is, unless context suggests otherwise, the distal portion, the distal section, or the distal length of the tissue-cutting device is not a terminal portion or terminal length of the tissue-cutting device.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method. Additionally, all embodiments disclosed herein are combinable and/or interchangeable unless stated otherwise or such combination or interchange would be contrary to the stated operability of either embodiment.

References to approximations may be made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Unless defined otherwise, all technical and scientific terms used herein have the same meaning as commonly understood by those of ordinary skill in the art.

Figure 1B:
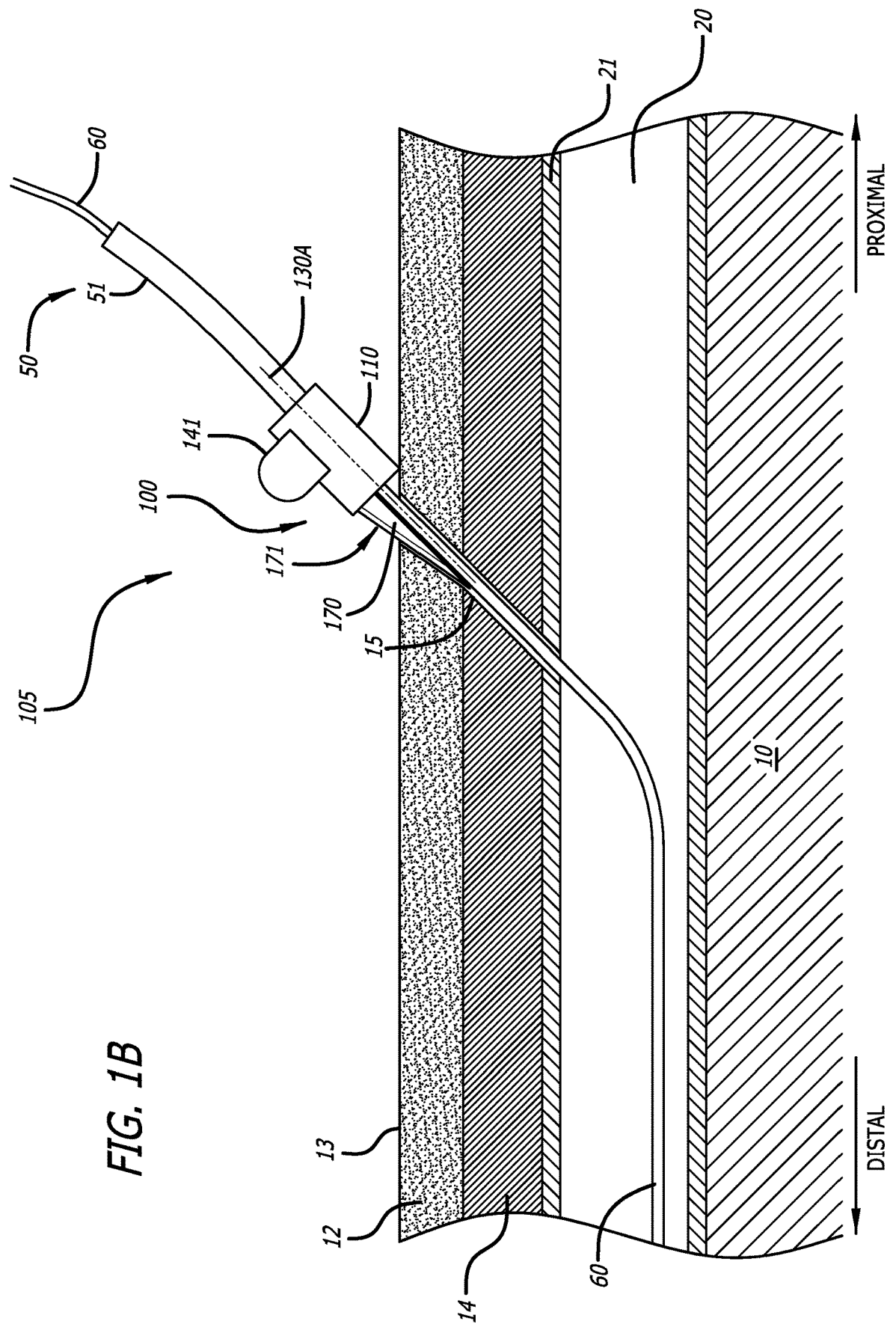
FIG. 1B illustrates the tissue-cutting device of FIG. 1A in use with a patient, in accordance with some embodiments.

FIGS. 1A-1B illustrate a tissue-cutting device 100. FIG. 1A is a perspective view of the tissue-cutting device (device) 100 coupled with a catheter 50 (e.g., a central venous catheter) having a guidewire 60 threaded through a lumen of the catheter 50. The device 100 is generally configured to enlarge a needle tract to accommodate insertion of the catheter 50 through the skin and into a vasculature of the patient. The device 100 generally includes a body 110 defining a distal end 111 and a proximal end 112. The device 100 may be coupled with the catheter 50 to define a catheter assembly 105. In some embodiments, the device 100 may be attached to the catheter 50 at a distal end of a catheter tube 51 of the catheter 50. In other embodiments of the catheter assembly 105, the device 100 may be attached to another location along the catheter tube 51, such as a tapered transition portion of the catheter tube 51 where the diameter of the catheter tube 51 is larger proximal the transition portion, for example.

The body 110 includes a channel 130 extending along a length of the body 110 from the distal end 111 and a proximal end 112, and the channel 130 is configured to receive the catheter tube 51 therein. The channel 130 defines a longitudinal axis 130A. The body 110 may be formed of a thermo-plastic material via an injection molding process.

The device 100 is generally configured to (i) inhibit lateral decoupling of the device 100 from the catheter 50 and/or the guidewire 60 in the absence of a deliberate action by the clinician and (ii) allow lateral decoupling of the device 100 from the catheter 50 and/or the guidewire 60 in response to the deliberate action by the clinician. More specifically, the body 110 is configured to laterally constrain the catheter tube 51 and/or the guidewire 60 within the channel 130 unless the clinician performs the deliberate action to allow lateral removal of the catheter tube 51 and/or the guidewire 60 from the channel 130. The channel 130 may allow longitudinal displace of the catheter tube 51 and/or the guidewire 60 within the channel 130 including longitudinal removal of the catheter tube 51 and/or the guidewire 60 from the channel 130. The body 110 is also configured to split along the length of the channel 130 in response to the deliberate action so that the catheter tube 51 and/or the guidewire 60 may be laterally removed from the channel 130 as further described below.

A tissue-cutting blade 170 having a cutting edge 171 is coupled with the body 110 so that the blade 170 extends distally away from the distal end 111 and so that the cutting edge 171 is disposed opposite the longitudinal axis 130A. The blade 170 is generally configured to nick or cut the skin and/or fascia in a radially outward direction from the needle tract 15. The cutting edge 171 is disposed at an angle 273 (see FIG. 2A) with respect to the longitudinal axis 130A so that a distal portion of the cutting edge 171 is positioned closer to the longitudinal axis 130A than a proximal portion of the cutting edge 171. As such a depth of cut by the blade 170 is generally defined by a depth of insertion of the device 100. The blade 170 may be formed of a stainless steel. In some embodiments, the blade 170 includes a sharp tip 172 at a distal end of the blade 170.

The body 110 includes one or more protrusions 141 extending laterally away from the body 110. The protrusions 141 may form a handle for the device 100, i.e., the clinician may grip and manipulate the device 100 and/or the catheter 50 via the protrusions 141. In the illustrated embodiment, the body 110 includes two protrusions 141. However, in other embodiments, the body 110 may include 1, 3, 4 or more protrusions 141. The protrusions 141 may be formed of any suitable shape to facilitate gripping and/or manipulating the device 100.

FIG. 1B is a side view of the device 100 disposed along a needle tract 15 of a patient 10. The catheter tube 51 is attached to the device 100 at the distal end of the catheter tube 51. The guidewire 60 is threaded through the catheter tube 51. The guidewire 60 is further threaded through the channel 130 of the device 100 and into the blood vessel 20 via the needle tract 15. As shown, the device 100 is generally configured for insertion within the needle tract 15 of the patient 10 extending between a skin surface 13 and a blood vessel wall 21 of the patient 10. The device 100 is also generally configured to enlarge the needle tract 15 by cutting the skin 12 and/or fascia 14 surrounding the needle tract 15. In some use cases, during insertion of the device 100 into the needle track 15, the device 100 is displaced along the guidewire 60, where the guidewire 60 provides a guide for the device 100.

In some embodiments, the body 110 or a portion thereof may define an insertion stop for the device 100 during insertion of the device 100 within the needle tract 15, i.e., during insertion, a portion of the body 110 may abut the skin surface 13 and prevent further insertion of the device 100. In some embodiments, the insertion stop may define a depth of cut for the blade 170 in accordance the angle 273 of the cutting edge 171.

FIG. 2A illustrates a side view of the device 100. The body 110 is cut away showing the catheter tube 51 disposed within the channel 130. The guidewire 60 is also shown extending through the catheter tube 51 and the channel 130. As stated above, the channel 130 is configured (i.e., sized and shaped) to receive the distal end of the catheter tube 51 therein, which distal end may include a taper. In some embodiments, the channel 130 may be configured to correspond to a shape of the distal end of the catheter tube 51. As such, the channel 130 may include a larger diameter portion 231 extending inward of the proximal end 112 of the body 110.

The channel 130 is also configured to receive the guidewire 60 therethrough. In some embodiments, the channel 130 may include a reduced diameter portion 232 that matches the diameter of the guidewire 60. In other words, the reduced diameter portion 232 may slidably receive the guidewire 60 while constraining the lateral position of the guidewire 60. More specifically, the reduced diameter portion 232 may constrain the lateral position of the guidewire 60 immediately adjacent the bottom edge 274 and/or the sharp point 172 of the blade 170. By constraining the sharp point 172 immediately adjacent the guidewire 60 during use, the propensity for skin or facial tissue to displace between the blade 170 and the guidewire 60 is minimized, i.e., the propensity for skin bridge is minimized. In other embodiments, the reduced diameter portion 232 may be omitted. In such an embodiment, the lateral position of the guidewire 60 may be constrained by the catheter tube 51.

In some embodiments, the catheter tube 51 may be bonded to the body 110 via an adhesive 210 (e.g., a pressure sensitive adhesive) to inhibit longitudinal displacement of the catheter tube 51 within the channel 130 in the absence of a deliberate action by the clinician. The bond may be configured to allow separation of body 100 from the catheter tube 51 in response to the deliberate action.

The blade 170 is shaped and positioned so that the cutting edge 171 of blade 170 is disposed at an angle 273 with respect to the longitudinal axis 130A of the channel 130. The angle 273 is defined so that a distal portion of the cutting edge 171 is closer to the longitudinal axis 130A than a proximal portion of the cutting edge 171. As such, the depth of cut by the cutting edge 171 may be defined by an insertion depth of the blade 170 into the needle tract 15. In some embodiments, the blade 170 (e.g., a proximal portion of the blade 170) may be insert-molded into the body 110 via the injection molding process of the body 110.

Figure 2C:
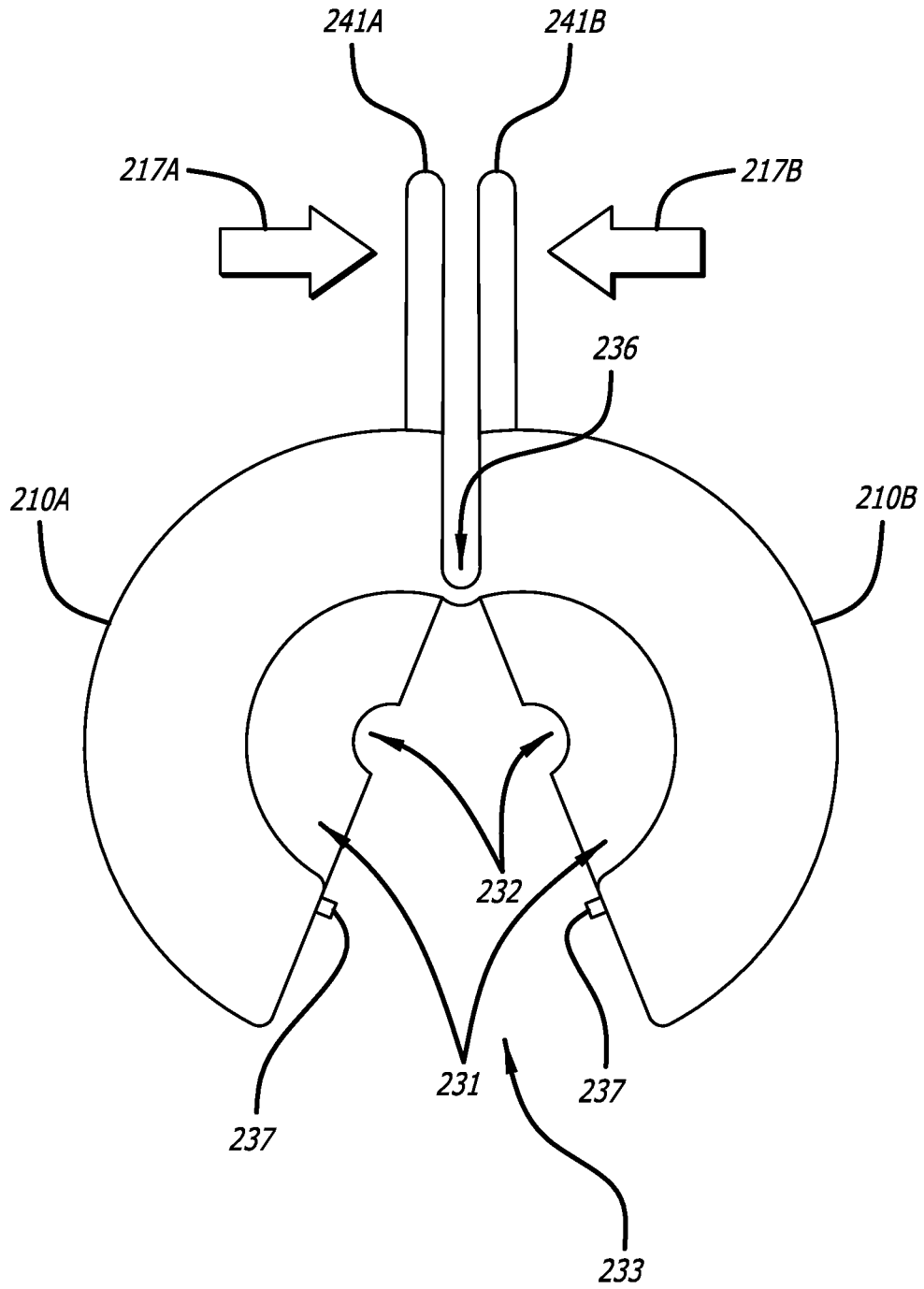
FIG. 2C is a back view of the tissue-cutting device of FIG. 1A disposed in an open state, in accordance with some embodiments.

FIGS. 2B and 2C illustrate a back view of the device 100 in a closed state and an open state, respectively. The body 110 includes a first body portion 210A and a second body portion 210B. The channel 130 is disposed between the first body portion 210A and a second body portion 210B. A longitudinally oriented hinge 236 couples the first body portion 210A with the second body portion 210B along a first side of the channel 130 such that the first body portion 210A is rotatable with respect to the second body portion 210B between the closed state (FIG. 2B), where the catheter tube 51 and/or guidewire 60 are laterally constrained within the channel 130 and the open state (FIG. 2C), where the catheter tube 51 and/or guidewire 60 are laterally removable from the channel 130 through the gap 233. The hinge 236 may be a living hinge formed via the injection molding process of the body 110.

In some embodiments, one or more frangible connecting members 237 may extend across the gap 233 between the first and second body portions 210A, 210B when the first and second body portions 210A, 210B are disposed in the closed position. The frangible connecting members 237 may prevent rotation of first body portion 210A with respect to the second body portion 210B, thereby preventing lateral removal of the catheter tube 51 and/or guidewire 60 from the channel 130, in the absence of the clinician performing the deliberate action. The deliberate action may include applying opposing forces 217A, 217B (e.g., a squeezing force) to the protrusions 241A, 241B, respectively to break the frangible connecting members 237 and rotate the first and second body portions 210A, 210B relative to each other to widen the gap 233 sufficiently to facilitate lateral removal of the catheter tube 51 and/or guidewire 60 from the channel 130 through the gap 233.

Figure 3A:
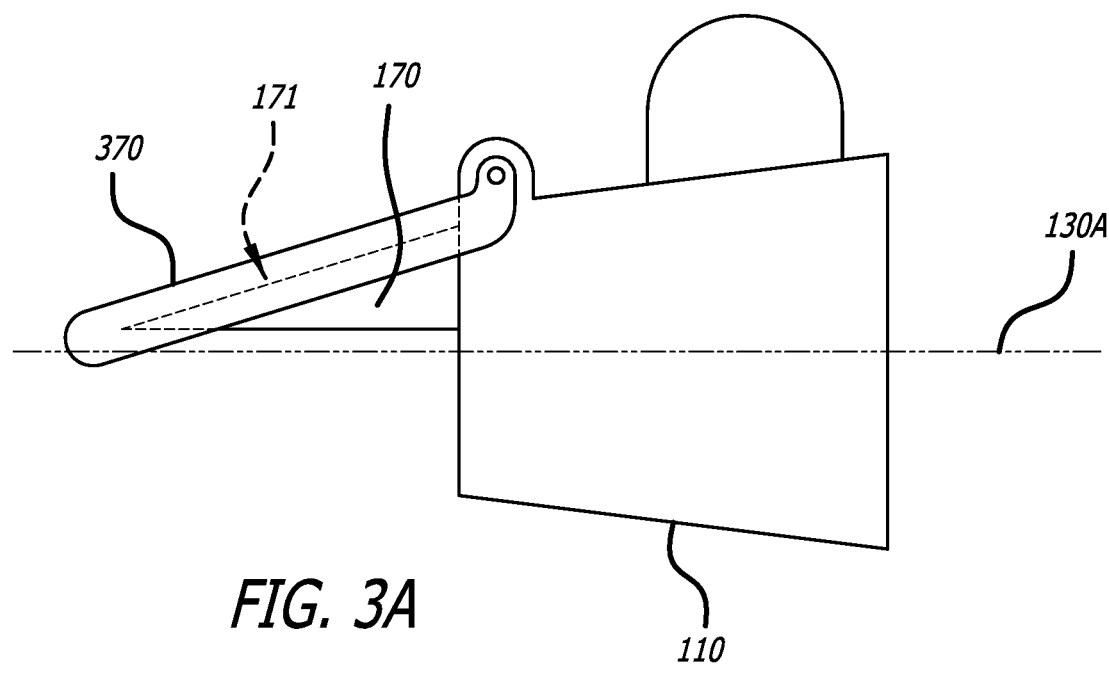
FIG. 3A illustrates the tissue-cutting device of FIG. 1A including an optional blade cover disposed in a safety position, in accordance with some embodiments.
Figure 3B:
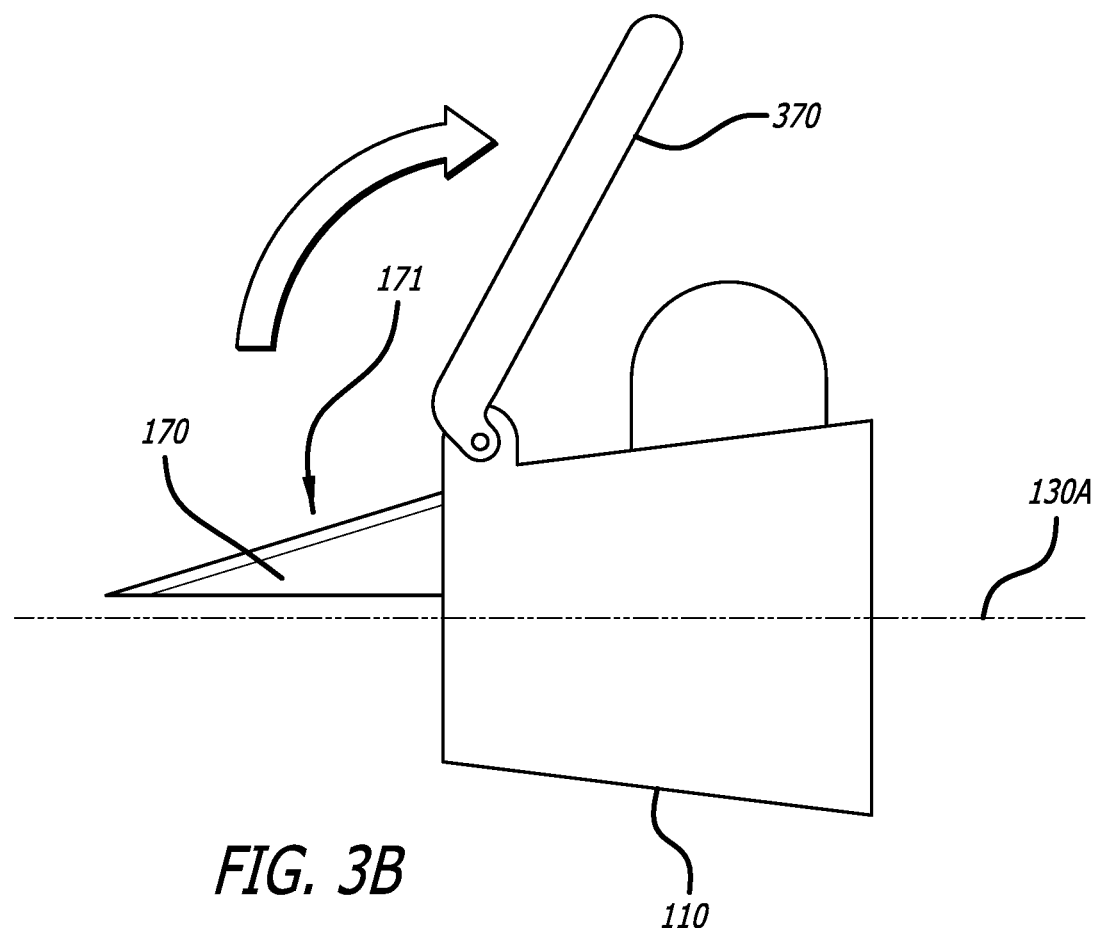
FIG. 3B illustrates the tissue-cutting device of FIG. 1A with the blade cover of FIG. 3A disposed in a use position, in accordance with some embodiments.

Referring to FIGS. 3A-3B, in some embodiments, the device 100 may optionally include a blade cover 370 for the blade 170, where the blade cover 370 is configured to prevent contact with the cutting edge 171 when the blade cover 370 is disposed in a safety position. FIG. 3A illustrates the blade cover 370 in the safety-position and FIG. 3B illustrates the blade cover 370 in a use-position. In some embodiments, the blade cover 370 may be rotatably coupled with the body 110 so that the blade cover 370 may be rotated between the safety-position and the use-position. In some embodiments, although not shown, the blade cover 370 may include a detent configured to maintain the blade cover 370 in the safety-position unless the clinician specifically transitions the blade cover 370 away from the safety-position. As may be appreciated by one of ordinary skill, the blade cover 370 may be coupled with the body 110 in any suitable fashion consistent with transitioning the blade cover 370 between a safety-position and a use-position.

Figure 4:
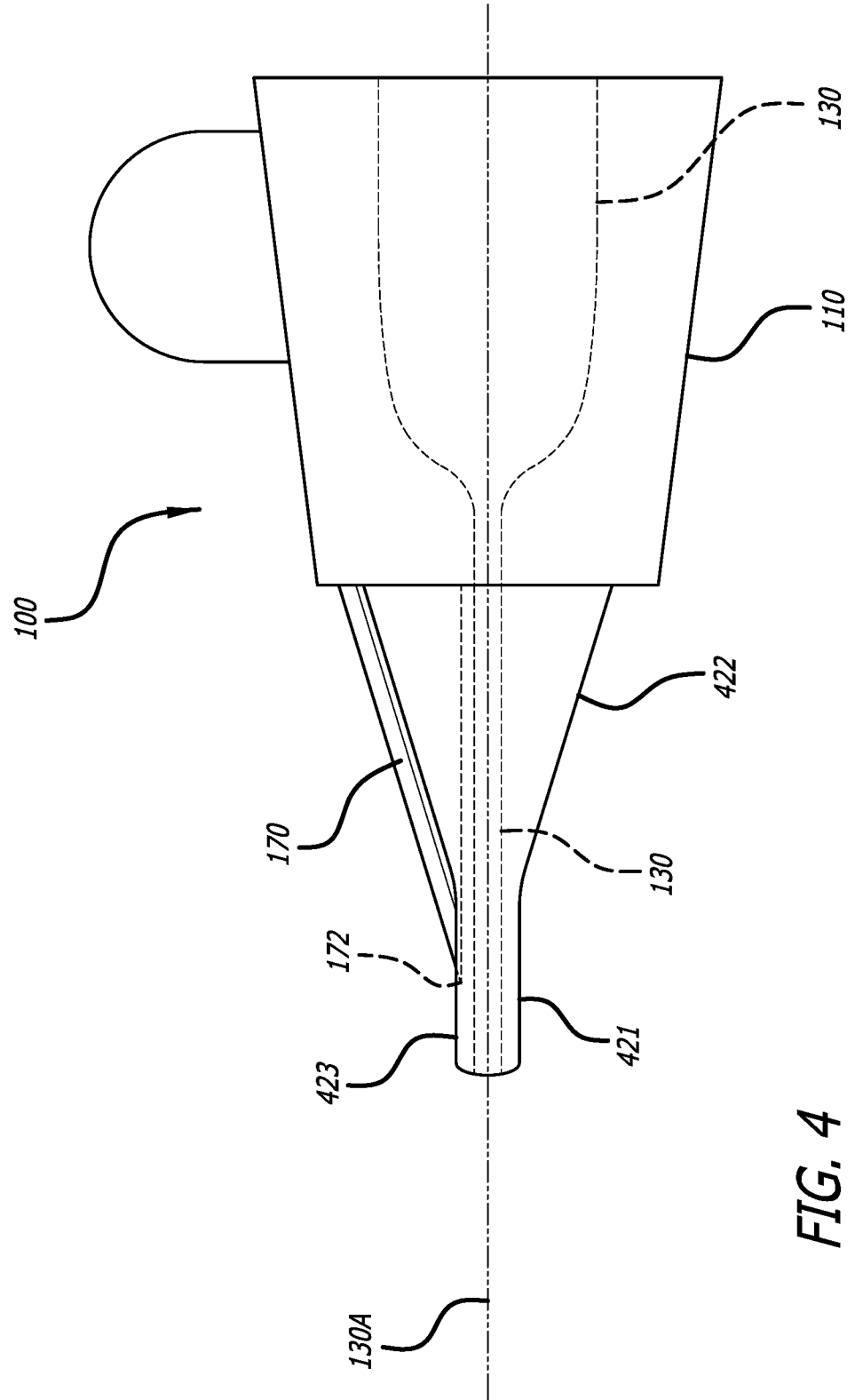
FIG. 4 illustrates the tissue-cutting device of FIG. 1A including an optional sheath extending distally away from a body of the tissue-cutting device, in accordance with some embodiments.

Referring to FIG. 4, in some embodiments, the device 100 may optionally include a sheath 421 coupled with the body 110 at the distal end 111 of the body 110 so that the sheath 421 extends along the blade 170. FIG. 4 illustrates a side view of the device 100 including the optional sheath 421. The sheath 421 is generally configured for insertion into the needle tract 15 along with the blade 170. The channel 130 extends along the sheath 421. In some embodiments, the sheath 421 includes a taper 422 configured to dilate the needle tract 15 during insertion of the sheath 421 into the needle tract 15. The sheath 121 may be integrally formed with the body 110. In use, the taper 422 may dilate the needle tract 15 in accordance with the blade 170 cutting the skin adjacent the needle tract 15. In some embodiments, the bottom edge 274 of the blade 170 and the sharp point 172 may be disposed within a wall 423 of sheath 421.

A method for placing a catheter into a vasculature of a patient, according to some embodiments, may include all or any subset of the following steps or processes. The method may be performed by a medical clinician in accordance with a medical treatment of the patient. The clinician may (i) insert a needle into the patient from a skin surface to a blood vessel lumen to define a needle tract, (ii) insert a guidewire into the vasculature of the patient via the needle tract, and (iii) advance the catheter along the guidewire. The catheter includes a catheter tube having the tissue-cutting device described above attached thereto. The clinician may further insert the tissue-cutting device into the needle tract, such that the blade of the tissue-cutting device cuts the skin adjacent the needle tract to enlarge the needle tract. After enlarging the needle tract, the clinician may laterally decouple the tissue-cutting device from the catheter tube and advance the catheter along the vasculature via the enlarged needle tract.

In some embodiments of the method, the clinician may insert the tissue-cutting device into the needle tract until the body of the tissue-cutting device abuts the skin surface so that the depth of the cut is limited by the limited insertion depth due to the insertion stop.

In some embodiments, the tissue-cutting device includes a sheath extending along the blade and as such, the clinician inserts the sheath into the needle tract.

In some embodiments of the method, the sheath includes a taper configured to dilate the needle tract during insertion of the sheath within the needle tract and the clinician may dilate the needle tract by inserting the sheath into the needle tract.

In some embodiments of the method, the device includes a blade cover selectively transitionable between a safety state and a use state, where the blade cover extends over the cutting edge in the safety state and the blade cover is disposed away from the cutting edge in the use state, and as such, the clinician may transition the blade cover from the safety state to the use state. In some embodiments, the blade cover may be rotatably coupled with the body, and as such, the clinician may rotate the blade cover away from the safety state toward the use state.

In some embodiments, the body includes a first body side coupled to a second body side via a longitudinally oriented hinge and the channel is disposed between the first body side and the second body side. According to such embodiments, rotation of the second body side with respect to the first body side transitions the channel between a closed state and an open state, where the catheter is laterally constrained within the channel in the closed state and the catheter is laterally removable from the channel in the open state.

In some embodiments of the method, the first body side includes a first lateral protrusion and the second body side includes a first lateral protrusion, and the clinician may apply a squeezing force to the first and second protrusions to transition the channel from the closed state to the open state. As such, the clinician may also laterally remove the catheter tube from the channel in the open state. The clinician may also laterally remove the guidewire from the channel in the open state.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A tissue-cutting device, comprising:
a body including a channel extending longitudinally between a distal end of the body and a proximal end of the body, wherein:
the body includes a first body side coupled to a second body side via a longitudinally oriented hinge,
the channel is disposed between the first body side and the second body side and is configured to receive a vascular catheter therein, the channel including a first diameter at the proximal end of the body and a second diameter at the distal end of the body, wherein the first diameter is greater than the second diameter,
rotation of the second body side with respect to the first body side transitions the channel between a closed state and an open state,
the vascular catheter is laterally constrained within the channel in the closed state, and
the vascular catheter is laterally removable from the channel in the open state; and
a tissue-cutting blade attached to the body, wherein the tissue-cutting blade:
extends distally away from the distal end of the body, and
extends laterally away from a longitudinal axis of the channel such that a cutting edge of the tissue-cutting blade is disposed opposite the longitudinal axis.

2. The device of claim 1, wherein the tissue-cutting device is configured for insertion along a needle tract extending between a skin surface and a blood vessel wall of a patient.

3. The device of claim 2, wherein the tissue-cutting blade is configured to enlarge the needle tract during insertion of the tissue-cutting device.

4. The device of claim 3, wherein the distal end of the body provides an insertion stop for the tissue-cutting device during insertion of the tissue-cutting device.

5. The device of claim 4, wherein the cutting edge of the tissue-cutting blade is disposed at an angle with respect to the longitudinal axis of the channel so that a distal portion of the cutting edge is closer to the longitudinal axis than a proximal portion of the cutting edge.

6. The device of claim 5, wherein the insertion stop defines a depth of cut for the tissue-cutting blade in accordance with the angle of the cutting edge.

7. The device of claim 1, wherein the body includes one or more protrusions extending laterally away from the body, the one or more protrusions defining a handle for the tissue-cutting device.

8. The device of claim 1, wherein the tissue-cutting blade is formed of a stainless steel.

9. The device of claim 1, wherein;

the body is formed of a thermo-plastic material via an injection molding process, and the tissue-cutting blade is insert-molded into the body.

10. The device of claim 1, wherein:

the body further includes a sheath extending distally away from the distal end, the sheath extends along the tissue-cutting blade, the channel extends along the sheath, and a sharp distal tip of the tissue-cutting blade is insert-molded into a wall of the sheath.

11. The device of claim 10, wherein the sheath includes a taper such that insertion of the sheath within a needle track dilates the needle track.

12. The device of claim 1, wherein the tissue-cutting device is configured to:

allow lateral decoupling of the tissue-cutting device from the vascular catheter in response to a deliberate action by a clinician, and inhibit lateral decoupling of the tissue-cutting device from the vascular catheter in an absence of the deliberate action by the clinician.

13. The device of claim 1, wherein the longitudinally oriented hinge is a living hinge formed via an injection molding process.

14. The device of claim 1, wherein:

the body includes:

a first protrusion extending away from the first body side; and a second protrusion extending away from the second body side, and applying a squeezing force to the first protrusion and the second protrusion transitions the channel from the closed state to the open state.

15. The device of claim 14, wherein:

the body includes one or more frangible connecting members extending between the first body side and the second body side at a location opposite the longitudinally oriented hinge, such that the one or more frangible connecting members constrain the channel in the closed state, and applying the squeezing force breaks the one or more frangible connecting members.

16. The device of claim 1, further comprising:

a blade cover selectively transitionable between a safety state and a use state, wherein the blade cover:

extends over the cutting edge in the safety state, and is disposed away from the cutting edge in the use state.

17. The device of claim 16, wherein:

the blade cover is rotatably coupled with the body, and transitioning the blade cover away from the safety state toward the use state includes rotating the blade cover.

18. The device of claim 17, wherein rotation of the blade cover away from the safety state is inhibited by a detent.

19. A catheter assembly, comprising:

a catheter configured for advancement along a vasculature of a patient, and the tissue-cutting device of claim 1 coupled with the catheter.

20. The assembly of claim 19, wherein the tissue-cutting device is attached to the catheter via an adhesive.

21. The assembly of claim 19, wherein the tissue-cutting device is attached to the catheter adjacent a diameter transition portion of the catheter.

22. The assembly of claim 19, wherein the tissue-cutting device is attached to the catheter adjacent a distal end of the catheter.

23. The assembly of claim 19, wherein, during use, manipulation of the catheter is facilitated by grasping the tissue-cutting device.

* * * * *